US009403878B2

(12) United States Patent
Wong et al.

(10) Patent No.: US 9,403,878 B2
(45) Date of Patent: Aug. 2, 2016

(54) METHODS FOR PRODUCING VIRUS PARTICLES WITH SIMPLIFIED GLYCOSYLATION OF SURFACE PROTEINS

(75) Inventors: Chi-Huey Wong, La Jolla, CA (US); Che Ma, New Taipei (TW); Yung-Chieh Tseng, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/883,752

(22) PCT Filed: Nov. 4, 2011

(86) PCT No.: PCT/US2011/059449
§ 371 (c)(1),
(2), (4) Date: Sep. 23, 2013

(87) PCT Pub. No.: WO2012/061776
PCT Pub. Date: May 10, 2012

(65) Prior Publication Data
US 2014/0011188 A1    Jan. 9, 2014

Related U.S. Application Data

(60) Provisional application No. 61/410,257, filed on Nov. 4, 2010.

(51) Int. Cl.
| | |
|---|---|
| A61K 39/145 | (2006.01) |
| C12N 7/00 | (2006.01) |
| C07K 14/005 | (2006.01) |
| C12P 21/00 | (2006.01) |
| A61K 39/12 | (2006.01) |

(52) U.S. Cl.
CPC ............ *C07K 14/005* (2013.01); *A61K 39/12* (2013.01); *A61K 39/145* (2013.01); *C12N 7/00* (2013.01); *C12P 21/005* (2013.01); *C12Y 302/01096* (2013.01); *C12N 2760/16111* (2013.01); *C12N 2760/16123* (2013.01); *C12N 2760/16134* (2013.01); *C12N 2760/16151* (2013.01); *G01N 2333/00* (2013.01); *G01N 2333/11* (2013.01); *Y02P 20/52* (2015.11)

(58) Field of Classification Search
CPC ..... A61K 39/145; A61K 39/12; A61K 39/42; A61K 2039/6075; A61K 38/162; C12N 7/00; C07K 14/005; C07K 16/1018; G01N 33/56983; G01N 2333/11
See application file for complete search history.

(56) References Cited

U.S. PATENT DOCUMENTS

| | | | |
|---|---|---|---|
| 2006/0121521 A1 | 6/2006 | Dowling et al. | |
| 2006/0188977 A1 | 8/2006 | Schwartz et al. | |
| 2010/0247571 A1 | 9/2010 | Wong et al. | |
| 2012/0219584 A1* | 8/2012 | Nabel et al. | 424/209.1 |

OTHER PUBLICATIONS

Schwarzer J, Rapp E, Hennig R, Genzel Y, Jordan I, Sandig V, Reichl U. Glycan analysis in cell culture-based influenza vaccine production: influence of host cell line and virus strain on the glycosylation pattern of viral hemagglutinin. Vaccine. Jul. 9, 2009;27(32):4325-36. Epub May 14, 2009.*
de Vries RP, de Vries E, Bosch BJ, de Groot RJ, Rottier PJ, de Haan CA. The influenza A virus hemagglutinin glycosylation state affects receptor-binding specificity. Virology. Jul. 20, 2010;403(1):17-25. Epub May 2, 2010.*
Wei CJ, Boyington JC, Dai K, Houser KV, Pearce MB, Kong WP, Yang ZY, Tumpey TM, Nabel GJ. Cross-neutralization of 1918 and 2009 influenza viruses: role of glycans in viral evolution and vaccine design. Sci Transl Med. Mar. 24, 2010;2(24):24ra21.*
Brug J, De Bock CA, Moed HD, Klein AJ. Antiviral action of derivatives of omega-aminoacetophenone. Br J Pharmacol Chemother. Dec. 1958;13(4):404-10.*
Millipore. MRCF0R030: Microcon-30kDa Centrifugal Filter Unit with Ultracef-30 membrane. Specification Sheet, Merck KGaA, Darmstadt, Germany, 2014.*
World Health Organization. WHO Expert Committee on Biological Standardization. Fifty-sixth Report. WHO, Geneva, Switzerland. 2007.*
De Vries et al., Glycan-dependent immunogenicity of recombinant soluble trimeric hemagglutinin. J Virol. Nov. 2012;86(21):11735-44. doi: 10.1128/JVI.01084-12. Epub Aug. 22, 2012.
Elbein et al., Kifunensine, a potent inhibitor of the glycoprotein processing mannosidase I., J Biol Chem. Sep. 15, 1990;265(26):15599-605.
Karaivanova et al., Processing of viral envelope glycoprotein by the endomannosidase pathway: evaluation of host cell specificity. Glycobiology. Jul. 1998;8(7):725-30.
Mishin et al., Effect of hemagglutinin glycosylation on influenza virus susceptibility to neuraminidase inhibitors. J Virol. Oct. 2005;79(19):12416-24.
Wang et al., Glycans on influenza hemagglutinin affect receptor binding and immune response. Proc Natl Acad Sci U S A. Oct. 27, 2009;106(43):18137-42. doi: 10.1073/pnas.0909696106. Epub Oct. 12, 2009.
WHO Manual on Animal Influenza Diagnosis and Surveillance, WHO/CDS/CSR/NCS/2002.5, Dec. 18, 1997, pp. 62-63.
Elbein et al., The effect of deoxymannojirimycin on the processing of the influenza viral glycoproteins. Arch Biochem Biophys. Dec. 1984;235(2):579-88.

* cited by examiner

*Primary Examiner* — Rachel B Gill
(74) *Attorney, Agent, or Firm* — Wolf, Greenfield & Sacks, P.C.

(57) ABSTRACT

Methods for producing virus particles with simplified glycosylation on structural or surface proteins, such as mono-glycosylated forms of influenza A virus, NIBRG-14 (H5N1). When used as targets for vaccine production, the conserved nature of such sites generates vaccines that are less sensitive to viral mutations. Such methods may include the use of glycosylation inhibitors for production of viruses with simplified glycosylation profiles.

18 Claims, 4 Drawing Sheets

A

NIBRG-14fg

B

NIBRG-14mg

A

B

METHODS FOR PRODUCING VIRUS PARTICLES WITH SIMPLIFIED GLYCOSYLATION OF SURFACE PROTEINS

CROSS-REFERENCE TO RELATED APPLICATIONS

This application is a U.S. national stage filing under section 371 of International Patent Application Ser. No. PCT/US2011/059449, filed Nov. 4, 2011 and which claims priority of U.S. Provisional Patent Application Ser. No. 61/410,257, filed Nov. 4, 2010 and titled "METHODS FOR PRODUCING MONO-GLYCOSYLATED INFLUENZA VIRUS HEMAGGLUTININ," the contents of which are incorporated herein in their entirety by reference.

TECHNICAL FIELD OF THE INVENTION

The present invention relates to viruses and in particular to the production of virus particles with simplified glycans. In particular, the present invention relates to the production of influenza virus particles with simplified glycosylation. Specifically, the invention relates to methods for production of mono-glycosylated influenza virus particles.

BACKGROUND OF THE INVENTION

The invention is disclosed herein in terms of the exemplary preparation of mono-glycosylated influenza viruses. It is contemplated, that the same methods can be used to prepare other viruses with simplified glycan structure including retroviruses such as the human immunodeficiency virus (HIV) and flaviviridae such as Dengue virus, West Nile virus, hepatitis C virus (HCV) and the like.

Influenza is caused by an RNA virus of the orthomyxoviridae family. There are three types of these viruses and they cause three different types of influenza: type A, B and C. Influenza virus type A viruses infect mammals (humans, pigs, ferrets, horses) and birds. This is very important to mankind, as this is the type of virus that has caused worldwide pandemics. Influenza virus type B (also known simply as influenza B) infects only humans. It occasionally causes local outbreaks of flu. Influenza C viruses also infect only humans. They infect most people when they are young and rarely cause serious illness.

Influenza A viruses infect a wide variety of mammals, including man, horses, pigs, ferrets and birds. The main human pathogen, associated with epidemics and pandemics. There are at least 15 known hemagglutinin (H) serotypes and 9 known neuraminidase (N) serotypes. Pigs and birds are believed to be particularly important reservoirs, generating pools of genetically and antigenically diverse viruses which get transferred back to the human population via close contact between humans and animals. Influenza B viruses infect mammals only and cause disease, but generally not as severe as A types. Unlike influenza A viruses, influenza B viruses do not have distinguishable serotypes. Influenza C viruses also infect mammals only, but rarely cause disease. They are genetically and morphologically distinct from A and B types.

There are 4 antigens present in the influenza virus, the hemagglutinin (HA), neuraminidase (NA), nucleocapsid (NA), the matrix (M) and the nucleocapsid proteins (NP). The NP is a type-specific antigen which occurs in 3 forms, A, B and C, which provides the basis for the classification of human influenza viruses. The matrix protein (M protein) surrounds the nucleocapsid and makes up 35-45% of the particle mass. Two surface glycoproteins are seen on the surface as rod-shaped projections. The hemagglutinin (HA) is initially synthesized as a trimeric precursor (HA0) containing three identical protein chains, each of which is proteolytically processed into two subunits, HA1 and HA2, that are held together covalently by a single disulfide bond. HA mediates the attachment of the virus to the cellular receptor. Neuraminidase (NA) molecules are present in lesser quantities in the envelope. Circulating human strains are notorious for their tendency to accumulate mutations from one year to the next and cause recurrent epidemics.

In eukaryotes, sugar residues are commonly linked to four different amino acid residues. These amino acid residues are classified as O-linked (serine, threonine, and hydroxylysine) and N-linked (asparagine). The O-linked sugars are synthesized in the Golgi or rough Endoplasmic Reticulum (ER) from nucleotide sugars. The N-linked sugars are synthesized from a common precursor, and subsequently processed. It is known that addition of N-linked carbohydrate chains is important for stabilization of folding, prevention of degradation in the endoplasmic reticulum, oligomerization, biological activity, and transport of glycoproteins. The addition of N-linked oligosaccharides to specific Asn residues plays an important role in regulating the activity, stability or antigenicity of mature proteins of viruses (Opdenakker G. et al *FASEB Journal* 7, 1330-1337 1993). It has also been suggested that N-linked glycosylation is required for folding, transport, cell surface expression, secretion of glycoproteins (Helenius, A., *Molecular Biology of the Cell* 5, 253-265 1994), protection from proteolytic degradation and enhancement of glycoprotein solubility (Doms et al., *Virology* 193, 545-562 1993). Viral surface glycoproteins are not only required for correct protein folding, but also provide protection against neutralizing antibodies as a "glycan shield." As a result, strong host-specific selection is frequently associated with codon positions of potential N-linked glycosylation. Consequently N-linked glycosylation sites tend to be conserved across strains and clades.

Outbreaks of influenza A virus continue to cause widespread morbidity and mortality worldwide. In the United States alone, an estimated 5 to 20% of the population is infected by influenza A virus annually, causing approximately 200,000 hospitalizations and 36,000 deaths. The establishment of comprehensive vaccination policies has been an effective measure to limit influenza morbidity. However, the frequent genetic drifting of the virus requires yearly reformulation of the vaccine, potentially leading to a mismatch between the viral strain present in the vaccine and that circulating. Thus, antiviral therapies against influenza virus are important tools to limit both disease severity as well as transmission.

The highly pathogenic H5N1 influenza viruses have caused outbreaks in poultry and wild birds since 2003 (Li K S et al. (2004) *Nature* 430:209-213). As of February 2010, these viruses have infected not only avian species but also over 478 humans, of which 286 cases proved to be fatal (www_who_int/csr/disease/avian_influenza/country/cases_table_2010_02_17/en/index.html). The highly pathogenic H5N1 and the 2009 swine-origin influenza A (H1N1) viruses have caused global outbreaks and raised a great concern that further changes in the viruses may occur to bring about a deadly pandemic (Garten R J, et al. (2009) *Science* 325:197-201, Neumann G, et al. (2009) *Nature* 459:931-939). There is great concern that an influenza virus would acquire the ability to spread efficiently between humans, thereby becoming a pandemic threat. An influenza vaccine must, therefore, be an integral part of any pandemic preparedness plan.

Important contributions to the understanding of influenza infections have come from the studies on hemagglutinin (HA), a viral coat glycoprotein that binds to specific sialylated glycan receptors in the respiratory tract, allowing the virus to enter the cell (Kuiken T, et al. (2006) *Science* 312: 394-397; Maines T R, et al. (2009) *Science* 325:484-487; Skehel J J, Wiley D C (2000) *Ann Rev Biochem* 69:531-569; van Riel D, et al. (2006) *Science* 312:399-399). To cross the species barrier and infect the human population, avian HA must change its receptor-binding preference from a terminally sialylated glycan that contains α2,3 (avian)-linked to α2,6 (human)-linked sialic acid motifs (Connor R J, et al. (1994) *Virology* 205:17-23), and this switch could occur through only two mutations, as in the 1918 pandemic (Tumpey™, et al. (2007) *Science* 315:655-659). Therefore, understanding the factors that affect influenza binding to glycan receptors is critical for developing methods to control any future crossover influenza strains that have pandemic potential.

The influenza virus hemagglutinin (HA) is a homotrimeric transmembrane protein with an ectodomain composed of a globular head and a stem region (Kuiken T, et al. (2006) *Science* 312:394-397). Both regions carry N-linked oligosaccharides (Keil W, et al. (1985) *EMBO J* 4:2711-2720), which affect the functional properties of HA (Chen Z Y, et al. (2008) *Vaccine* 26:361-371; Ohuchi R, et al. (1997) *J Virol* 71:3719-3725). HA is the virion surface glycoprotein that attaches the virus to its receptors on host cells and fuses the viral envelope with the membranes of endocytic vesicles to initiate the infectious process. (Crecelius D. M., et al. (1984) *Virology* 139, 164-177). It is also the virion component that stimulates the formation of protective antibodies. The nature and extent of glycosylation of the HA have been implicated in altering its receptor binding properties and in the emergence of viral variants with enhanced cytopathogenicity (Aytay S., Schulze I. T. (1991) *J. Virol.* 65, 3022-3028) and virulence (Deshpande K. L., et al. (1987) *Proc. Natl. Acad. Sci. U.S.A.* 84, 36-40) and in masking its antigenic sites (Skehel J. J., et al. (1984) *Proc. Natl. Acad. Sci. U.S.A.* 81, 1779-1783). Mutational deletion of HA glycosylation sites can affect viral receptor binding (Gunther I, et al. (1993) *Virus Res* 27:147-160).

The amino acid sequence of the HA and hence the location of its N-glycosylation sites is determined by the viral genome. The structures of these oligosaccharides appear to be determined by their position on the HA (Keil W., et al. (1985) *EMBO J.* 4, 2711-2710) and by the biosynthetic and trimming enzymes provided by the host cell in which the virus is grown. The plasticity of the viral genome and the host-specified glycosylation machinery can, together, create virus populations that are more heterogeneous in structure and function than could be developed by either process alone. This diversity is considered to be responsible for survival of these viruses and for their ability to overcome the inhibitory effects of neutralizing antibodies and antiviral agents.

The HA appears to have regions that must be glycosylated, others that must be free of oligosaccharides, and still others in which glycosylation may be either advantageous or detrimental to the survival of the virus. Glycosylation sites at certain positions on the HA of influenza A viruses isolated from various animals and humans are highly conserved and therefore appear to be essential for the formation and/or maintenance of functional HA (Gallagher P. J., et al. (1992) *J. Virol.* 66, 7136-7145). Conversely, the generation of glycosylation sites in certain regions of the HA reduces its transport to the cell surface, and its stability and/or function (Gallagher P., et al. (1988) *J. Cell Biol.* 107, 2059-2073). It is in the regions in which glycosylation is neither prohibited nor required for the formation of functional HA that oligosaccharide diversity may have a major selective effect, depending on the specific environment in which the virus is expected to grow.

Changes in the peptide sequence at or near glycosylation sites may alter HA's 3D structure, and thus receptor-binding specificity and affinity. Indeed, HAs from different H5N1 subtypes have different glycan-binding patterns (Stevens J, et al. (2008) *J Mol Biol* 381:1382-1394). Mutagenesis of glycosylation sites on H1 and H3 has been studied in the whole-viral system (Chandrasekaran A, et al. (2008) *Nat Biotechnol* 26:107-113; Deom C M, et al. (1986) *Proc Natl Acad Sci USA* 83:3771-3775). Changes in glycosylation could affect receptor-binding specificity and affinity, especially with regard to the most pathogenic H5N1 HA.

Less highly glycosylated or non-glycosylated regions of hemagglutinin continue to mutate to escape from the host immune system. Vaccine design using monoglycosylated HA is disclosed in US Pat. App. Pub. No. 2010/0247571 (Wong et al.). Thus, there is a need for novel and efficient methods for production of monoglycosylated influenza virus particles.

SUMMARY OF THE INVENTION

The disclosure herein provides exemplary demonstration of producing mono-glycosylated influenza viruses. The disclosed methods are equally applicable to the production of viruses with simplified glycans on the structural proteins. Conserved regions of structural proteins with high glycosylation can be targeted for vaccine design once the glycosylation patterns present at these sites are simplified to mono, di-, tri-, or other glycosylated regions.

Specifically, there is a need for cross neutralizing monoclonal antibodies that can be used in the design and validation of vaccine production processes that maintain or enhance the quality and antigenicity of cross neutralizing epitopes in current and future manufactured vaccines. Assuming that antibody binding to antigen is reflective of structural integrity and antigenic potential, one would attempt binding of cross neutralizing antibodies, such as monoglycosylated HA polypeptides and quantitatively assess their cross neutralizing potential. Vaccines derived against monglycolyslated derivatives of influenza HA are expected to increase immunogenicity towards universal epitopes.

The antigen is generated by partially removing sugars from the viral glycoprotein to expose the glycosylation sites (which are highly conserved and do not mutate or do not mutate aggressively) and at the same time retain adequate sugars to preserve the tertiary structure of the glycoprotein. The partially glycosylated viral glycoproteins are generated by partially deglycosylating the glycoproteins such that a particular glycosylation site retains one, two or three sugar units. In some aspects the partially glycosylated glycoprotein can be generated by providing a protein or polypeptide unglycosylated at one or more particular glycosylation sites and conjugating a mono-, di- or tri-saccharide to the glycosylation sites.

A vaccine is disclosed comprising at least one partially glycosylated HA glycoprotein and a pharmaceutically acceptable carrier. In some implementations, the partially glycosylated HA glycoprotein is selected from the group consisting of partially glycosylated influenza virus H1, H3, and H5.

A method is disclosed comprising administering to a subject susceptible of influenza a vaccine comprising at least one deglycosylated HA glycoprotein and a pharmaceutically acceptable carrier. In some implementations, the deglycosylated HA glycoprotein is selected from the group consisting of Hl, H3, and H5.

In some implementations the deglycosylation leaves a monoglycosylation (one sugar remaining) at one or more glycosylation site on the glycoprotein. In some implementations the deglycosylation leaves a diglycosylation (2 sugars remaining) at least one glycosylation site on the glycoprotein. In some implementations the deglycosylation leaves a triglycosylation (3 sugars remaining) at one or more glycosylation site on the glycoprotein. In some implementations the deglycosylation leaves at least one of a monoglycosylation, a diglycosylation and a triglycosylation at at least one glycosylation site on the glycoprotein.

In some embodiments, the influenza HA antigen is recombinantly produced in a cell culture. The cell culture comprises MDCK cells, Vero cells or PER.C6 cells. The kifunensine is added to the host cell harboring a recombinant influenza HA antigen.

In some aspects, the inhibition of α-mannosidase I results in glycoproteins with $Man_9(GlcNAc)_2$.

In other embodiments, the influenza HA antigen comprises a whole influenza virus. The whole influenza virus is grown in a specific pathogen free (SPF) embryonated chicken egg host.

Then, kifunensine is added to the allantoic cavity of specific pathogen free (SFP) embryonated chicken egg.

In some aspects, the kifunensine is added at a concentration of 0.005 to 0.5 mg/ml.

The recovered influenza virus HA antigen is treated with about 0.1 to about 100 µg/mL EndoH.

In some aspects, the monoglycosylated influenza virus is isolated by a method comprising density gradient ultracentrifugation.

In some aspects, the method further comprises purifying the monoglycosylated influenza virus HA antigen by a method comprising ultrafiltration. In some embodiments, the ultrafiltration comprises use of a 0.2 µm filter.

In some aspects, the method further comprises analyzing the monoglycosylated influenza virus by electron microscopy.

In some aspects, the method further comprises quantifying the monoglycosylated influenza virus by a method comprising treatment with PNGase. In some aspects, the method further comprises quantifying the monoglycosylated influenza virus by a method comprising SDS-PAGE electrochromatography.

In some aspects, the method further comprises analyzing the glycan composition of the isolated monoglycosylated influenza virus by a method comprising mass spectrometry.

The invention relates to a monoglycosylated influenza virus HA antigen (whole virus or recombinant) prepared by any method disclosed herein.

The invention relates to the use of a monoglycosylated influenza virus HA antigen (whole virus or recombinant) prepared by any method disclosed herein, for the preparation of a vaccine.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

(FIG. 1A) The virus was grown in different concentration of N-glycosylation processing inhibitor, kifunensine. (FIG. 1B) High-mannose glycosylated virus was digested to Mono-glycosylated virus by different concentration of Endo H. (FIG. 1C) Compared with purified fully-glycosylated virus, purified mono-glycosylated virus has obvious downshift in both HA1 and HA2. These samples were analyzed by Western blot analysis using an anti-H5 HA rabbit anti-serum.

(FIG. 2A) Fully-glycosylated NIBRG-14. (FIG. 2B) Mono-glycosylated NIBRG-14. The virus particles was stained by 2% methylamine tungstate and analyzed by transmission electron microscopy.

(FIG. 4A) Glycosylation sites of NIBRG-14 Hemagglutinin are labeled with amino-acid residue numbers. The structure was created with PDB code 1jsm, and glycosylation site was colored in red. (FIG. 4B) Glycopeptide analysis of mono-glycosylated NIBRG-14 hemagglutinin. After Endo H digestion, most of glycosylation sites are mono-glycosylated, except that glycosylation sites 295 and 489 are still partially (<10%) high-mannose glycosylated.

DETAILED DESCRIPTION OF THE INVENTION

Figure 1:
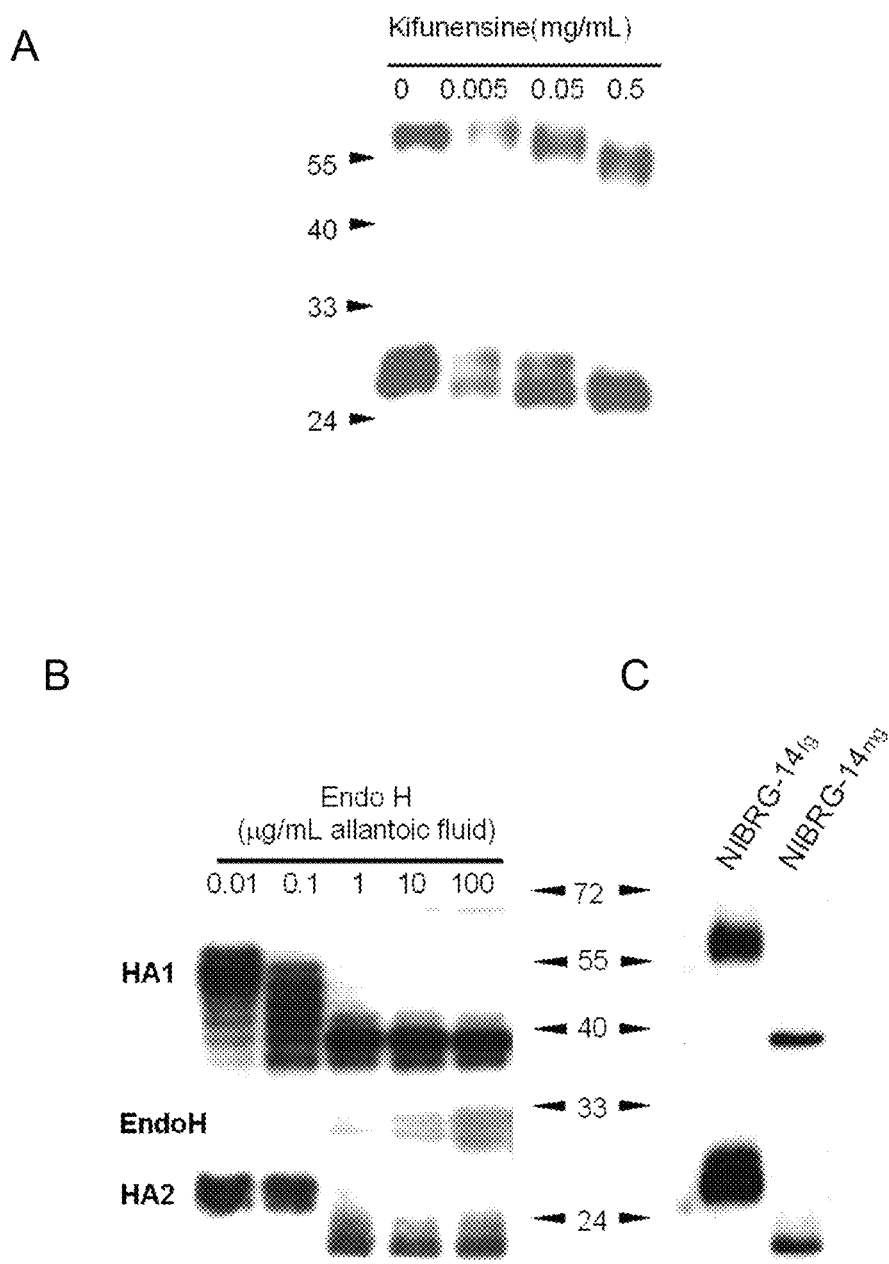
FIG. 1 shows the preparation of Mono-glycosylated NIBRG-14 virus.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control. The following references provide one of skill with a general definition of many of the terms used in this invention: Singleton et al., Dictionary of Microbiology and Molecular Biology (2nd Ed. 1993); The Cambridge Dictionary of Science and Technology (Walker ed., Cambridge University Press. 1990); The Glossary of Genetics, 5th ed., R. Rieger et al. (eds.), Springer Verlag (1991); and Hale & Margham, The Harper Collins Dictionary of Biology (1991).

Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The terms "influenza A subtype" or "influenza A virus subtype" are used interchangeably, and refer to influenza A virus variants that are characterized by a hemagglutinin (H) viral surface protein, and thus are labeled by an H number, such as, for example, H1, H3, and H5. In addition, the subtypes may be further characterized by a neuraminidase (N) viral surface protein, indicated by an N number, such as, for example, N1 and N2. As such, a subtype may be referred to by both H and N numbers, such as, for example, H1N1, H5N1, and H5N2. The terms specifically include all strains (including extinct strains) within each subtype, which usually result from mutations and show different pathogenic profiles. Such strains will also be referred to as various "isolates" of a viral subtype, including all past, present and future isolates. Accordingly, in this context, the terms "strain" and "isolate" are used interchangeably. Subtypes contain antigens based upon an influenza A virus. The antigens may be based upon a hemagglutinin viral surface protein and can be designated as "HA antigen". In some instances, such antigens are based on the protein of a particular subtype, such as, for example, an H1 subtype and an H5 subtype, which may be designated an H1 antigen and an H5 antigen, respectively.

As used in the present disclosure, the term "deglycosylated" or "partially glycosylated" protein denotes a protein that has one or more sugars removed from the glycan structure of a fully glycosylated instance of the protein and in which the protein substantially retains its native conformation/folding. A "deglycosylated" protein includes a partially glycosylated protein in which the deglycosylation process leaves a monoglycosylation, a diglycosylation or a triglycosylation at one or more glycosylation sites present on the glycoprotein.

A "partially glycosylated" protein includes a "deglycosylated" protein in which one or more sugars are retained at each glycosylation site, and each partial glycosylation site contains a smaller glycan structure (containing fewer sugar units) as compared to the site in a fully glycosylated instance of the glycoprotein, and the partially glycosylated protein substantially retains its native conformation/folding. A "partially glycosylated" protein is generated by partial deglycosylation of the glycan structure of at least one glycosylation site of a fully glycosylated instance of the glycoprotein. A "partially glycosylated" protein also is generated by introducing glycosylation at an unglycosylated site of a protein such that the added glycosylation sequence is smaller than the glycan structure at that site in a fully glycosylated instance of the glycoprotein. A "partially glycosylated" protein also is generated by synthesizing a viral glycoprotein sequence, or fragment thereof, introducing glycosylated amino acid units (e.g., GlcNAc-Arginine moieties) at glycosylation sites of the sequence, such that the added glycan structure is smaller than the glycan structure at that site in a fully glycosylated instance of the glycoprotein.

Viral transmission begins with a critical interaction between hemagglutinin (HA) glycoprotein, which is on the viral coat of influenza, and sialic acid (SA) containing glycans, which are on the host cell surface. To elucidate the role of HA glycosylation in this important interaction, various defined HA glycoforms were prepared, and their binding affinity and specificity were studied by using a synthetic SA microarray. Truncation of the N-glycan structures on HA increased SA binding affinities while decreasing specificity toward disparate SA ligands. The contribution of each monosaccharide and sulfate group within SA ligand structures to HA binding energy was quantitatively dissected. It was found that the sulfate group adds nearly 100-fold (2.04 kcal/mol) in binding energy to fully glycosylated HA, and so does the biantennary glycan to the monoglycosylated HA glycoform. Antibodies raised against HA protein bearing only a single N-linked GlcNAc at each glycosylation site showed better binding affinity and neutralization activity against influenza subtypes than the fully glycosylated HAs elicited. Thus, removal of structurally nonessential glycans on viral surface glycoproteins is a very effective and general approach for vaccine design against influenza and other human viruses.

Glycosylation of polypeptides is typically either N-linked or O-linked. N-linked refers to the attachment of the carbohydrate moiety to the side chain of an asparagine residue. A "sequon" is a sequence of three consecutive amino acids in a protein that can serve as the attachment site to a polysaccharide (sugar) called an N-linked-Glycan. This is a polysaccharide linked to the protein via the nitrogen atom in the side chain of asparagine (Asn). A sequon is either Asn-$X_{aa}$-Ser or Asn-$X_{aa}$-Thr, where $X_{aa}$ is any amino acid except proline. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. While the sequon Asn-X-Ser/Thr is absolutely required for the attachment of N-linked oligosaccharides to a glycoprotein (Marshall R D, *Biochemical Society Symposia* 40, 17-26 1974), its presence does not always result in glycosylation and some sequons in glycoproteins can remain unglycosylated. (Curling E M, et al., *Biochemical Journal* 272, 333-337 1990)

One aspect of the present invention is a method of producing non-native glycoproteins having simplified carbohydrate structures.

Accordingly the method is applicable to retroviruses such as HIV, flaviviruses such as hepatitis C, Dengue and West Nile, and the like.

Approximately half of the molecular mass of gp120, the receptor-binding envelope protein of human immunodeficiency virus (HIV), consists of N-linked glycans. Nearly half of these glycans are of the high mannose type. These high mannose glycans furnish a rich forest of mannose residues on the virus surface making HIV a prime target for interaction with mannose-specific lectins of the immune system.

Hepatitis C virus (HCV) envelope glycoproteins are highly glycosylated, with generally 4 and 11 N-linked glycans on E1 and E2, respectively. Several glycans play an important role in HCVcc assembly and/or infectivity. At least five glycans on E2 (denoted E2N1, E2N2, E2N4, E2N6, and E2N11) strongly reduce the sensitivity of HCV to antibody neutralization. (Helle F et al., *J Virol.* 2010 November; 84(22): 11905-15).

The E protein of most flaviviruses is modified by Asn-linked glycosylation at residue 153/154 and in the case of the four dengue virus (DENV) serotypes by a second glycan at residue 67. In Dengue virus, the N-linked glycans on the E protein are a mix of high-mannose and complex glycans. The West Nile virus envelope (E) protein contains a single N-linked glycosylation site at residue 154. Since ablation of glycans at these sites markedly reduce. but do not eliminate, infectivity, vaccines targeted at the conserved sites when they are presented with simplified glycosylation can lead to effective therapy that is less sensitive to mutational variations in the virus.

Glycosidase Inhibitors

Glycoside hydrolases (also called glycosidases or glycosyl hydrolases) catalyze the hydrolysis of the glycosidic linkage to release smaller sugars. They are common enzymes with roles in nature including degradation of biomass such as cellulose and hemicellulose, in anti-bacterial defense strategies (e.g., lysozyme), in pathogenesis mechanisms (e.g., viral neuraminidases) and in normal cellular function (e.g., trimming mannosidases involved in N-linked glycoprotein biosynthesis). Together with glycosyltransferases, glycosidases form the major catalytic machinery for the synthesis and breakage of glycosidic bonds.

Inhibitors of glycosylation are contemplated for use according to the methods of the invention. Examples of such inhibitors include Kinefusine, Australine, Castanospermine, Deoxynojirimycin, Deoxymannojirimycin, Swainsoninne, Mannostatin A, and the like.

Australine is a polyhydroxylated pyrrolizidine alkaloid that is a good inhibitor of the alpha-glucosidase amyloglucosidase (50% inhibition at 5.8 microM), but it did not inhibit beta-glucosidase, alpha- or beta-mannosidase, or alpha- or beta-galactosidase. Castanospermine is an indolizine alkaloid that inhibits alpha-glucosidase activities and alters glycogen distribution. Castanospermine inhibits dengue virus infection (Whitby K et al., *J Virol.* 2005 July; 79(14): 8698-8706).

The biosynthesis of the various types of N-linked oligosaccharide structures involves two series of reactions: 1) the formation of the lipid-linked saccharide precursor, $Glc_3Man_9$ (GlcNAc)2-pyrophosphoryl-dolichol, by the stepwise addition of GlcNAc, mannose and glucose to dolich01-P; and 2) the removal of glucose and mannose by membrane-bound glycosidases and the addition of GlcNAc, galactose, sialic acid, and fucose by Golgi-localized glycosyltransferases to produce different complex oligosaccharide structures.

Use of inhibitors that block the modification reactions at different steps, cause the cell to produce glycoproteins with altered carbohydrate structures. A number of alkaloid-like compounds have been identified that are specific inhibitors of the glucosidases and mannosidases involved in glycoprotein processing. These compounds cause the formation of glycoproteins with glucose-containing high mannose structures, or various high-mannose or hybrid chains, depending on the site of inhibition. (Elbein A D *FASEB J.* 1991 December; 5(15): 3055-3063).

The first four enzymes that function in the processing of N-linked glycoproteins are glycosidases. GlcNAc-phosphotransferase catalyzes the first step in the synthesis of the mannose 6-phosphate determinant. A proper carbohydrate structure greatly facilitates the efficient phosphorylation by GlcNAc-phosphotransferase. The carbohydrate structure coupled to phosphorylation is necessary for the synthesis of a mannose-6-phosphate signal on the GAA molecule is a high mannose N-glycan.

Several mannosidase processing inhibitors are known. Swainsonine, isolated from locoweed was shown to be a potent inhibitor of the Golgi mannosidase II, but to have no effect on mannosidase 1(James, L. F., Elbein, A. D., Molyneux, R. J., and Warren, C. D. (1989) Swainsonine and related glycosidase inhibitors. Iowa State Press, Ames, Iowa). Deoxymannojirimycin is a fairly potent inhibitor of rat liver mannosidase I. In intact cells, deoxymannojinimycin blocked the synthesis of complex types of N-linked oligosaccharides and caused the accumulation of glycoproteins having $Man_{7-9}(GlcNAc)_2$ structures, with $Man_9(GlcNAc)_2$ oligosaccharides predominating (Elbein, A. D., et al. (1984) *Arch. Biochem. Biophys.* 235, 579-588). Mannostatin A is a metabolite produced by the microorganism, *Streptoverticillium verticillus*, and this compound was reported to be a potent inhibitor of rat epididymal α-mannosidase. (Aoyagi, T., et al. (1989) *J. Antibiot.* 42, 883-889).

Kifunensine (Kif) was first isolated from the actinomycete, *Kitasatosporia kifunense* No. 9482 (M. Iwami, O. et al. *J. Antibiot.*, 40, 612, 1987) and is a cyclic oxamide derivative of 1-amino-mannojirimycin. Kifunensine inhibits the animal Golgi enzyme, mannosidase I. When kifunensine is added to cultured mammalian cells at concentrations of 1 μg/ml or higher, it causes a complete shift in the structure of the N-linked oligosaccharides from complex chains to $Man_9$ $(GlcNAc)_2$ structures, in keeping with its inhibition of mannosidase I. On the other hand, deoxymannojirimycin, even at 50 μg/ml, does not prevent the formation of all complex chains (Elbein, A. D., et al. (1990) Kifunensine, a potent inhibitor of the glycoprotein processing mannosidase I. *J Biol. Chem.* 265, 15599-15605). Thus, kifunensine is one of the most effective glycoprotein processing inhibitors.

Kifunensine has also shown promising immunomodulatory activity in α-mannosidase inhibition. The synthesis of kifunensine has been reported by both Fujisawa Pharmaceutical Co. (H. Kayakiri, et al., *Tetrahedron Lett.*, 31, 225, 1990; H. Kayakiri, et al., *Chem. Pharm. Bull.*, 39, 1392, 1991) and Hudlicky et al. (J. Rouden and T. Hudlicky, *J. Chem. Soc. Perkin Trans.* 1, 1095, 1993; J. Rouden, T. et al., *J. Am. Chem. Soc.*, 116, 5099, 1994).

Treating cells with kifunensine (Kif) results in the inhibition of glycoprotein processing in those cells (Elbein et al (1991) *FASEB J* (5):3055-3063; and Bischoff et al (1990) *J. Biol. Chem.* 265(26):15599-15605). Kif blocks complex sugar attachment to modified proteins. However, if sufficient Kif is utilized to completely inhibit glycoprotein processing on lysosomal hydrolases, the resultant hydrolases have mannose-9 structures, which are not the most efficient substrates for the GlcNAc phosphotransferase enzyme.

According to the invention, a glycosidase inhibitor such as Kif, is added to the cells in the amount of at least 0.01 μg/ml to about at least 500 μg/ml, including 0.25, 0.5, 0.75, 1.0, 1.25, 1.5, 1.75, 2.0, 2.5, 3.0, 3.5, 4.0, 4.5, 5.0, 5.5, 6.0, 6.5, 7.0, 7.5, 8.0, 8.5, 9.0, 9.25, 9.5, 9.75 and all values there between.

Kifunensine inhibits the function of the enzyme a-mannosidase I in the N-glycosylation pathway and results in glycoproteins with $Man_9GlcNAc_2$ compositions.

Levels and/or types of complex carbohydrate structures can be measured using known methods. For example, glycoproteins and their associated oligosaccharides can be characterized using endoglycosidases to differentiate between high mannose and complex type oligosaccharides (Maley et al (1989) Anal. Biochem. 180:195-204). Peptide-$N_4$-(N-acety 162-glucosaminyl)asparagine amidase (PNGaseF) is able to hydrolyze asparagines-linked (N-linked) oligosaccharides at the β-aspartylglycosylamine bond to yield ammonia, aspartic acid and an oligosaccharide with an intact di-N-acetylchitobiose on the reducing end. The specificity of PNGase is broad because high mannose, hybrid, di-, tri- and tetraantennary complex, sulfated and polysialyl oligosaccharides are substrates. Additionally, endo-β-N-acetylglucosaminidase H (EndoH) effectively hydrolyzes the chitobiose unit in hybrid- and mannose-containing N-linked oligosaccharides possessing at three mannose residues, providing that the α-1,6-mannose arm has another mannose attached. Complex oligosaccharides are resistant to EndoH digestion.

To characterize the type of N-linked oligosaccharides present in glycoproteins, an aliquot of protein can be digested with PNGaseF (0.5% SDS, 1% β-mercaptoethanol, 50 mM NP-40, 50 mM Sodium Phosphate, pH 7.5) or EndoH (0.5% SDS, 1% β-mercaptoethanol, 50 mM Sodium Citrate, pH 5.5) under reducing conditions. The native and digested proteins are then analyzed by SDS-polyacrylamide electrophoresis under reducing conditions and the relative mobilities compared. If the glycoprotein contains only high mannose oligosaccharides the PNGaseF and EndoH treated samples will have a greater mobility than the untreated protein. The EndoH treated protein will have a slightly higher molecular weight due to the single remaining N-acetylglucosamine at each N-linked glycosylation site. If a glycoprotein contains only complex oligosaccharides, the EndoH treated protein will not have a shift in migration compared to the untreated protein. If there are both complex and high mannose oligosaccharides, then EndoH treated protein will be smaller than the non-treated glycoprotein but larger than the PNGaseF treated protein. The difference will be greater than that which can be accounted for by the remaining N-acetylglucosamine.

To generate the simplified glycans on the target glycoproteins, endoglycosidases are used. An endoglycosidase is an enzyme that releases oligosaccharides from glycoproteins or glycolipids. Or it merely cleaves polysaccharide chains between residues that are not the terminal residue, although releasing oligosaccharides from conjugated protein and lipid molecules is more common. It breaks the glycosidic bonds between two sugar monomers in a polymer. Examples of endoglycosidases include, but are not limited to, endoglycosidase D, endoglycosidase F, endoglycosidaseF1, endoglycosidaseF2, endoglycosidase H, and endoglycosidase S.

Preparing Mono-glycosylated Influenza Virus

To produce proteins with high mannose glycoproteins, the cells harboring influenza virus are exposed to Kif (and/or DMJ) to inhibit glycoprotein processing. To produce mono-glycosylated influenza virus, the virus is injected into the allantoic cavity of pathogen-free embryonated chicken eggs with a mannosidase inhibitors, such as kifunensine.

Kifunensine inhibits the function of the enzyme α-mannosidase I in the N-glycosylation pathway and results in glycoproteins with $Man_9(GlcNAc)_2$ compositions. Concentration of kifunensine in inhibiting glycosylation of hemagglutinin ranges between 5, 10, 25, 50, 75, 100, 200, 500 μg/mL and up to 500 μg/mL and all values there between.

Following about 1-3 days of incubation, the kifunensine treated allantoic fluid is harvested and digested with endoglycosidase (Endo H) to remove high-mannose type glycans, i.e., concentrations able to convert from $Man_9(GlcNAc)_2$ to single GlcNAc. Concentration of Endo H in the allantoic fluid to produce mono-glycosylated hemagglutinin ranges at least about 0.1, 0.5, 1, 2, 5, 7, 10, 20, 30, 40, 50, 60, 75, 100, 150, 200, 500 or more μg/mL of allantoic fluid.

Subsequently, the mono-glycosylated virus is recovered and purified.

Use of Mono-glycosylated Influenza Virus

The herein disclosed mono-glycosylated influenza virus antigens can be used to immunize against influenza virus infection. The specific virus from which the antigens are derived may be the same as or different from the specific virus for which protection is being provided, because cross-protection between different isolates is known to occur with influenza viruses, particularly within the same viral subtypes.

The influenza vaccines currently in use are designated whole virus (WV) vaccine or subvirion (SV) (also called "split" or "purified surface antigen"). The WV vaccine contains intact, inactivated virus, whereas the SV vaccine contains purified virus disrupted with detergents that solubilize the lipid-containing viral envelope, followed by chemical inactivation of residual virus. Attenuated viral vaccines against influenza are also in development. A discussion of methods of preparing conventional vaccine may be found in Wright, P. F. & Webster, R. G., FIELDS VIROLOGY, 4d Ed. (Knipe, D. M. et al. Ed.), 1464-65 (2001), Where a vaccine includes more than one strain of influenza, the different strains are typically grown separately and are mixed after the viruses have been harvested and antigens have been prepared. Alternatively, different segments of different isolates of the influenza virus may be combined to generate a multipotent vaccine. The influenza virus(es) used in the processes of the invention may be reassortant strains, and/or may have been obtained by reverse genetics techniques. The virus(es) may be attenuated. The virus(es) may be temperature-sensitive. The virus(es) may be cold-adapted. A reassortant strain including the HA and/or NA viral segments from a pathogenic strain and the remaining six or seven segments from a non-pathogenic strain may be used.

The influenza virus antigen used in the immunogenic composition according to the invention may be in the form of a live virus or, preferably, an inactivated virus. Virus inactivation typically involves treatment with a chemical such as formalin or β-propiolactone. Where an inactivated virus is used, the antigen may be a whole virus, a split virus, or viral subunits. Split viruses are obtained by treating virions with detergents (e.g. ethyl ether, polysorbate 80, deoxycholate, tri-N-butyl phosphate, Triton X-100, Triton N101, cetyltrimethylammonium bromide, etc.) to produce subvirion preparations. Subunit vaccines comprise one or both of the influenza surface antigens hemagglutinin and neuraminidase. Influenza antigens can also be presented in the form of virosomes.

Where an antigen is prepared from an influenza virus (i.e. rather than having been produced in a recombinant or synthetic system that does not involve growth of influenza viruses), the virus may be grown either on eggs or in cell culture. Growth in specific pathogen-free embryonated eggs is the traditional route by which influenza viruses have been grown for vaccine production, and cell culture is a more recent development. Where cell culture is used then the influenza virus vaccine will typically be grown on mammalian cells, such as MDCK cells, Vero cells or PER.C6 cells. These cell lines are widely available e.g. from the American Type Cell Culture (ATCC) collection, or from the Coriell Cell Repositories (Camden, N.J.). For example, the ATCC supplies various different Vero cells under catalog numbers CCL-81, CCL-81.2, CRL-1586 and CRL-1587, and it supplies MDCK cells under catalog number CCL-34. Growth on avian cell lines, including cell lines derived from hen, e.g. chicken embryo fibroblasts (CEF), is also possible.

Likewise, a virus (such as HIV, HCV, Dengue virus, influenza virus, flavivirus and the like) can be grown in cell culture in the presence of one or more glycosidase inhibitors (such as Kinefusine, Australine, Castanospermine, Deoxynojirimycin, Deoxymannojirimycin, Swainsoninne, Mannostatin A, and the like). Cell culture systems for growth of these viruses are well known in the art. West Nile virus can be grown in monkey kidney epithelial cell or chick embryo cell tissue culture. HIV can be cultivated in peripheral blood mononuclear cells (PBMC) culture. HC can be grown in cells derived from the human hepatoma cell line Huh-7.

Immunogenic and medicament compositions of the invention are suitable for administration to a patient. This can be achieved by various ways, including but not limited to: intradermal injection; transdermal administration; and topical administration. These may be used in conjunction with skin abrasion e.g. by emery paper or by the use of microabrasives.

Immunogenic and medicament compositions of the invention are preferably presented as vaccines.

Compositions of the invention may include an adjuvant. Adjuvants that have been used in influenza vaccines include aluminum salts, chitosan, CpG oligodeoxynucleotides such as CpG 7909, oil-in-water emulsions such as MF59, water-in-oil-in-water emulsions, *E. coli* heat labile toxin and its detoxified mutants, monophosphoryl lipid A and its 3-O-deacylated derivative, pertussis toxin mutants, muramyl dipeptides, etc.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Preparation of the Fully-Glycosylated and Mono-Glycosylated Viruses

The influenza A virus, NIBRG-14 (H5N1) (Nicolson C, et al. (2005) *Vaccine* 23(22):2943-2952), was injected (1000 TCID50 (50% Tissue Culture Infective Dose) in 200 µl PBS) into the allantoic cavity of 10-days-old specific pathogen free (SFP) embryonated chicken eggs to produce the ordinary fully-glycosylated virus (WHO (2005) *WHO manual on animal influenza diagnosis and surveillance*. (World Health Organization, Geneva)).

To produce mono-glycosylated virus, the virus was injected into the allantoic cavity with 0.2 mg/ml kifunensine (Cayman Chemical). Kifunensine inhibits the function of the enzyme α-mannosidase I in the N-glycosylation pathway and results in glycoproteins with Man9GlcNAc2 compositions (Elbein A D, et al. (1990) *J Biol Chem* 265(26):15599-15605).

Concentration dependence of kifunensine to inhibit glycosylation of hemagglutinin was analyzed (FIG. 1A). After 3 days of incubation, the allantoic fluid was harvested and centrifuged to remove the debris for 10 min at 3,000 g. The kifunensine treated allantoic fluid was then digested with endoglycosidase Endo H (20 µg per ml allantoic fluid) for 12 hour at 4° C. to remove high-mannose type glycans, i.e., from Man9GlcNAc2 to single GlcNAc. Concentration dependence of Endo H in the allantoic fluid to produce mono-glycosylated hemagglutinin was analyzed (FIG. 1B).

Subsequently, the mono-glycosylated virus was pelleted by ultracentrifuge for 90 min at 46,000 g, resuspended with PBS and purified by a discontinuous sucrose density gradient (25%, 40%) for 90 min at 270,000 g. The virus in the gradient was collected and pelleted by ultracentrifuge for 90 min at 120,000 g. Finally, the pellet was resuspended in PBS and filtered by 0.22 µm filter (CDC (1982) *Concepts and Procedures for Laboratory-based Influenza Surveillance* (U.S. Dept. of Health and Human Services., Washington, D.C.); Harvey R, et al. (2008) *Vaccine* 26(51):6550-6554). Compared with purified fully-glycosylated virus, purified mono-glycosylated virus has obvious downshifts in both HA1 and HA2 (FIG. 1C).

Example 2

Figure 2:
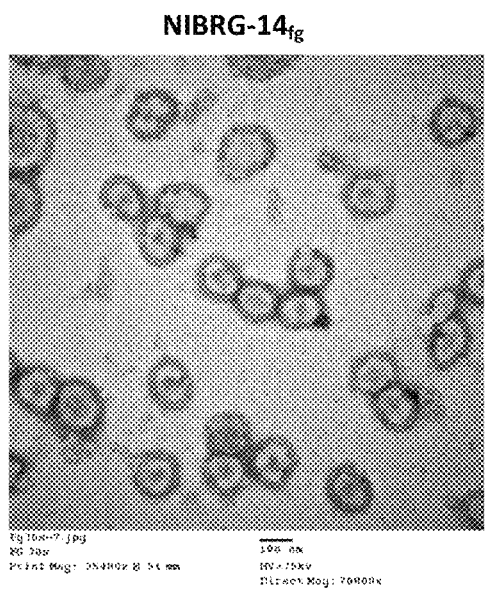
FIG. 2 shows the electron micrographs of fully-glycosylated and mono-glycosylated viruses.
Figure 2:
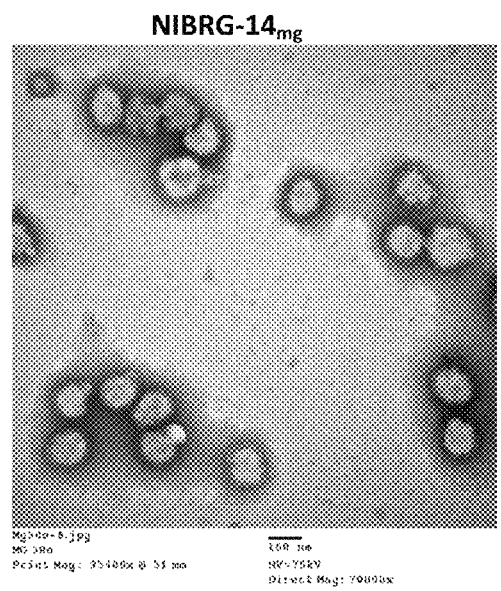

Electron Microscopy Analysis of the Fully-Glycosylated and Mono-Glycosylated Viruses The virus solution was placed on the collodion-carbon-coated surface of a copper grid (Electron Microscopy Sciences). Excess fluid was removed with filter paper, and 2% methylamine tungstate (Ted Pella, Inc.) was added to stain for 30 sec. Excess fluid was removed with filter paper, and washed by $H_2O$ for 30 sec. Then, the grid was air-dried for 4 hour and the virus particles were photographed by transmission electron microscopy (Hitachi H-7000). The fully-glycosylated and mono-glycosylated influenza NIBRG-14 viruses are similar in size and morphology (FIG. 2).

Example 3

Quantification of Hemagglutinin in the Virus

Figure 3:
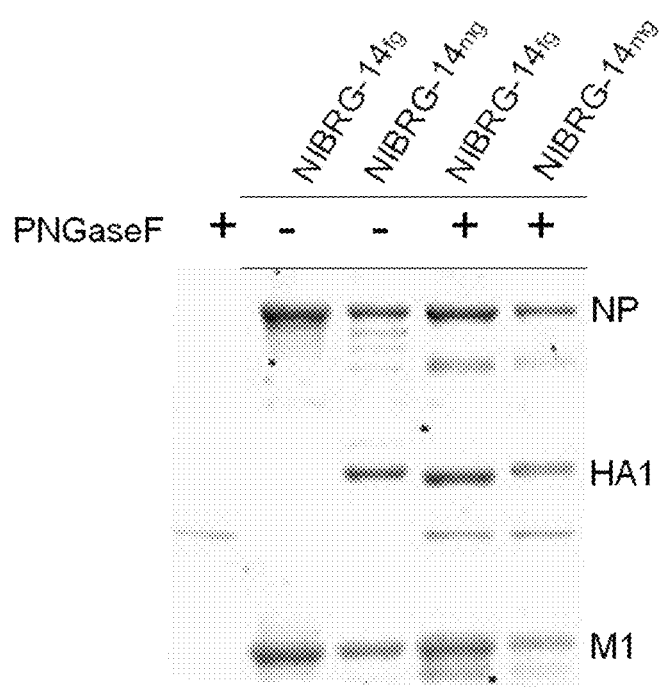
FIG. 3 shows the quantification of Hemagglutinin. The amount of hemagglutinin of NIBRG-14 virus was determined by intensity of PNGase F deglycosylated HA1 in SDS-PAGE.

The virus was mixed with denature buffer (5% SDS and 10% β-mercaptoethanol) and boiled for 10 min, then the sample was added 10% NP-40 and treated with PNGase F (New England Biolabs) at 25° C. for overnight. The sample was mixed with SDS-PAGE sample buffer and heated to 95° C. for 10 min prior to loading to the gel. The gel was stained by SYPRO RUBY® (Invitrogen) and analyzed by VERSA DOC® imaging system (Bio-rad). The treatment of PNGase F prior to SDS-PAGE analysis is to separate HA1 from NP protein in the fully-glycosylated virus sample. This enables direct intensity comparison of HA1 proteins from both fully-glycosylated and mono-glycosylated viruses on SDS-PAGE for quantification of hemagglutinin in the virus (FIG. 3).

Example 4

Glycopeptide analysis with LC-MS-MS

Figure 4:
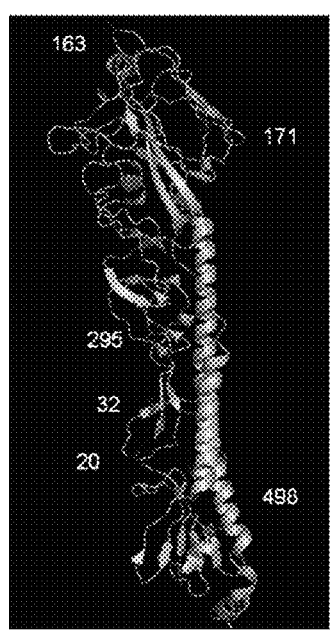
FIG. 4 shows glycopeptide analysis of mono-glycosylated NIBRG-14 hemagglutinin.
Figure 4:
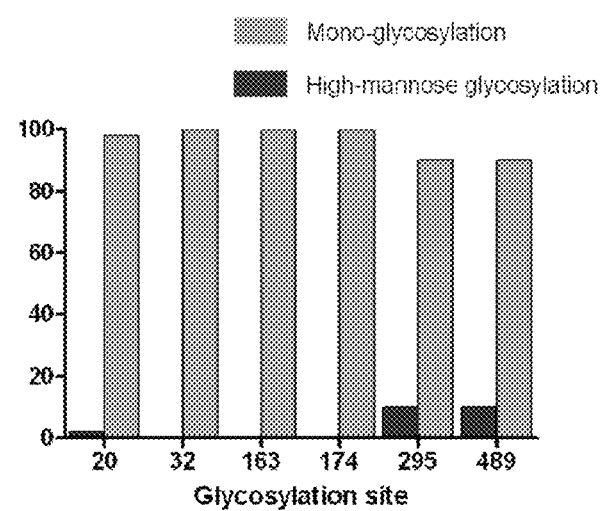

Mass spectrometry was used to analyze the glycan composition of the mono-glycosylated virus. The virus solution was mixed with non-reducing sample buffer and heated to 95° C. for 10 min prior to loading to the gel. The gel was stained by Commassie blue. The HA0 band was cut to small piece for in-gel tryptic digestion with trypsin. After the digestion, sample was analyzed by LC-MS-MS (Wu Y, et al. (2010) *Rapid Commun Mass Spectrom* 24(7):965-972) (Agilent Technologies, Thermo Scientific). There are six N-glycosylation sites of influenza NIBRG-14 virus. Except for small percentage of presence of high-mannose type glycans in residue 295 (~10% $Man_6(GlcNAc)_2$) and residue 489 (~10% $Man_{7-9}(GlcNAc)_2$), all other glycans are mono-glycosylated with single GlcNAc saccharide residue attached (FIG. 4).

All publications and patent applications cited in this specification are incorporated herein by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing an immunogenic composition, the method comprising:
    a) producing an influenza virus hemagglutinin (HA) antigen in an in vitro cell culture or embryonated egg with an effective amount of a mannosidase inhibitor, wherein the concentration of the mannosidase inhibitor is sufficient to inhibit .alpha.-mannosidase I in the N-glycosylation pathway;
    b) contacting the influenza virus HA antigen recovered from step a) with endoglycosidase H (Endo H), wherein the concentration of Endo H is sufficient to remove high mannose type glycans;
    c) isolating a monoglycosylated influenza virus HA antigen produced in step b); and
    d) producing an immunogenic composition comprising the monoglycosylated influenza virus HA antigen of (c) and a pharmaceutically acceptable carrier and/or an adjuvant.

2. The method of claim 1, wherein the HA antigen is derived from an H5N1 influenza virus.

3. The method of claim 2, wherein the H5N1 influenza virus is NIBRG-14.

4. The method of claim 1, wherein the mannosidase inhibitor is kifunensine (Kif) or deoxymannojirimycin (DMJ).

5. The method of claim 1, wherein the cell culture comprises MDCK cells, Vero cells or PER.C6 cells.

6. The method of claim 1, wherein the inhibition of a-mannosidase I result in glycoproteins with $Man_9(GlcNAc)_2$.

7. The method of claim 1, wherein the influenza HA antigen is part of a whole influenza virus grown in a specific pathogen free (SPF) embryonated chicken egg host.

8. The method of claim 7, wherein the mannosidase inhibitor is added to an allantoic cavity of the specific pathogen free (SPF) embryonated chicken egg.

9. The method of claim 1, wherein the mannosidase inhibitor is added to the host cell harboring a recombinant influenza HA antigen.

10. The method of claim 4, wherein the kifunensine is added at a concentration of 0.005 to 0.5 mg/ml.

11. The method of claim 7, wherein the influenza HA antigen is recovered by a process comprising:
    incubating for a time sufficient to grow the influenza virus;
    collecting an allantoic fluid from the allantoic cavity of the SPF embryonated chicken egg comprising the influenza virus; and
    isolating the influenza virus that comprises the influenza HA antigen.

12. The method of claim 11, wherein the recovered influenza virus HA antigen is treated with about 0.1 to about 100μg/mL Endo H to produce an influenza virus comprising a monoglycosylated HA antigen.

13. The method of claim 12, wherein the influenza virus comprising a monoglycosylated HA antigen is isolated by a method comprising density gradient ultracentrifugation.

14. The method of claim 1, further comprising purifying the monoglycosylated influenza virus HA antigen by a method comprising ultrafiltration.

15. The method of claim 1, further comprising analyzing the monoglycosylated influenza virus by electron microscopy.

16. The method of claim 1, further comprising quantifying the monoglycosylated influenza virus HA antigen by a method comprising treatment with PNGase.

17. The method of claim 1, further comprising analyzing the glycan composition of the isolated monoglycosylated influenza virus HA antigen by a method comprising mass spectrometry.

18. The method according to claim 1, wherein the influenza virus HA antigen is selected from the group consisting of influenza virus H1, H3, and H5 glycoproteins.

* * * * *